United States Patent
Bhavsar et al.

(10) Patent No.: US 11,246,862 B2
(45) Date of Patent: Feb. 15, 2022

(54) PROCESS FOR THE PREPARATION OF LIFITEGRAST

(71) Applicant: MANKIND PHARMA LTD., New Delhi (IN)

(72) Inventors: Jigar Tarun Kumar Bhavsar, Gurugram (IN); Rakesh Tiwari, Gurugram (IN); Bhuwan Bhashkar, Gurugram (IN); Anil Kumar, Gurugram (IN)

(73) Assignee: MANKIND PHARMA LTD., New Delhi (IN)

( * ) Notice: Subject to any disclaimer, the term of this patent is extended or adjusted under 35 U.S.C. 154(b) by 17 days.

(21) Appl. No.: 16/754,312

(22) PCT Filed: Sep. 20, 2018

(86) PCT No.: PCT/IB2018/057235
§ 371 (c)(1),
(2) Date: Apr. 7, 2020

(87) PCT Pub. No.: WO2019/073325
PCT Pub. Date: Apr. 18, 2019

(65) Prior Publication Data
US 2020/0306242 A1    Oct. 1, 2020

(30) Foreign Application Priority Data
Oct. 10, 2017 (IN) .............................. 201711035902

(51) Int. Cl.
*A61K 31/4725* (2006.01)
(52) U.S. Cl.
CPC ...... *A61K 31/4725* (2013.01); *C07B 2200/13* (2013.01)
(58) Field of Classification Search
CPC .................. A61K 31/4725; C07B 2200/13
See application file for complete search history.

(56) References Cited

U.S. PATENT DOCUMENTS

| | | | |
|---|---|---|---|
| 7,314,938 B2 | 1/2008 | Shen et al. | |
| 8,080,562 B2 | 12/2011 | Burnier et al. | |
| 8,367,701 B2 | 2/2013 | Burnier et al. | |
| 8,378,105 B2 | 2/2013 | Burnier | |
| 9,085,553 B2 | 7/2015 | Zeller et al. | |
| 2008/0018283 A1 | 1/2008 | Kachouh et al. | |
| 2015/0033693 A1 | 2/2015 | Ito et al. | |
| 2015/0336939 A1* | 11/2015 | Zeller ................. | C07D 405/06 514/307 |

OTHER PUBLICATIONS

International Search Report, issued in the corresponding PCT application No. PCT/IB2018/057235, dated Dec. 21, 2018, 3 pages.
Mino R. Caira, "Crystalline Polymorphism of Organic Compounds", Design of Organic Solids, Topic in current chemistry, Springer Verlag, Berlin, vol. 198, Jan. 1, 1998, 46 pages.

* cited by examiner

*Primary Examiner* — Timothy R Rozof
(74) *Attorney, Agent, or Firm* — Hamre, Schumann, Mueller & Larson, P.C.

(57) ABSTRACT

The present invention relates to a novel process for the preparation of lifitegrast of Formula I. The present invention further provides a novel process for the purification of lifitegrast of Formula I.

Formula I

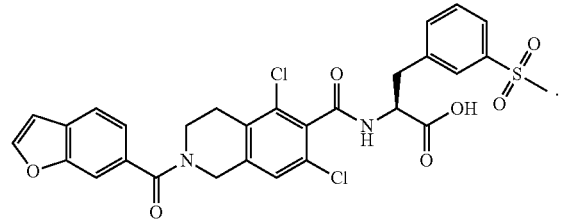

6 Claims, 2 Drawing Sheets

PROCESS FOR THE PREPARATION OF LIFITEGRAST

FIELD OF THE INVENTION

Figure 1:
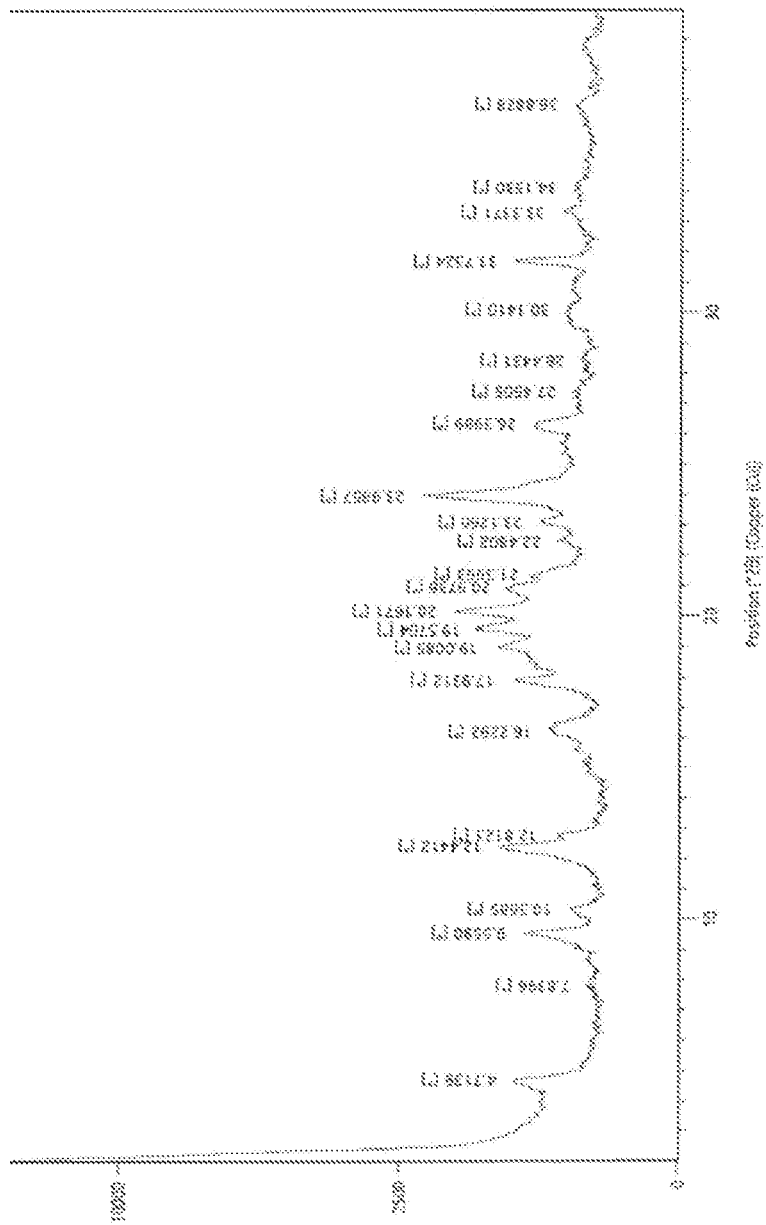

The present invention relates to a novel process for the preparation of lifitegrast of Formula-I and process for purification thereof.

Formula-I

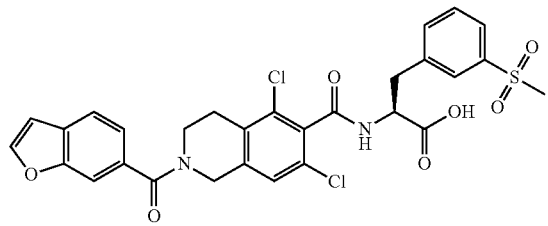

BACKGROUND OF THE INVENTION

Lifitegrast, chemically known as (S)-2-(2-(benzofuran-6-carbonyl)-5,7-dichloro-1,2,3,4-tetrahydroisoquinoline-6-carboxamido)-3-(3-(methylsulfonyl)phenyl) propanoic acid, approved by the USFDA under the brand name Xiidra for the treatment of dry eye disease (DED). Lifitegrast is generically disclosed in U.S. Pat. No. 7,314,938.

U.S. Pat. Nos. 8,080,562 and 8,378,105 discloses process for the preparation of lifitegrast as mentioned in the scheme below:

Scheme 1

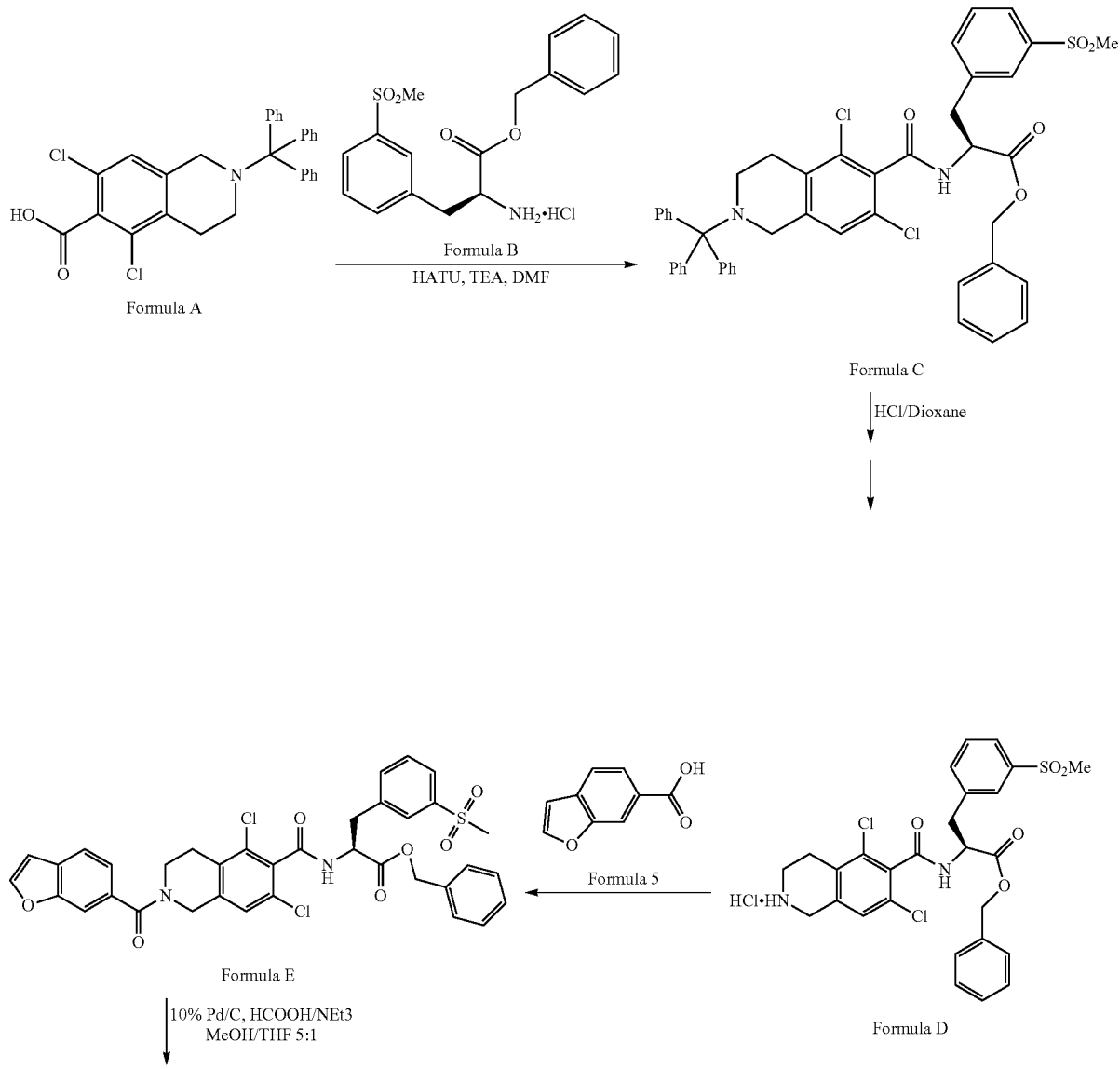

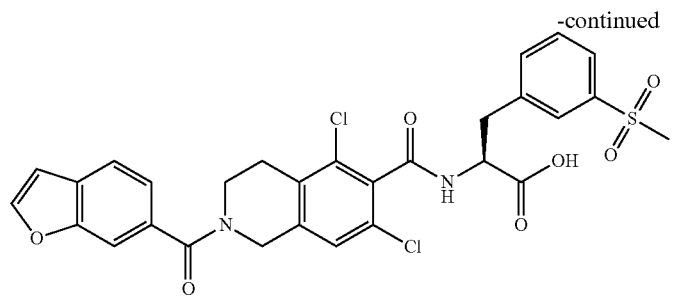

Formula I

U.S. Pat. No. 8,080,562 also discloses crystalline forms A-E as well as amorphous form of lifitegrast and their process of preparation. U.S. '562 discloses preparation of Form A by slurrying amorphous form of lifitegrast in methyl ethyl ketone or acetonitrile. It further discloses that various crystalline forms can be prepared from Form A such as crystalline Form B is prepared by suspending the crystalline Form A in ethyl acetate; crystalline Form C is prepared by suspending crystalline Form A in ethanol; and crystalline Form D is prepared by suspending crystalline form A in water.

U.S. Pat. No. 8,367,701 discloses process of recrystallization of lifitegrast by slurrying lifitegrast in methyl ethyl ketone or acetonitrile followed by filtering and washing with water.

U.S. Pat. No. 9,085,553 discloses a process of recrystallization of lifitegrast from solution comprising acetone, preferably aqueous acetone. It also discloses an alternate method for preparing lifitegrast which includes preparation of lifitegrast ester followed by hydrolysis of said ester as shown in the scheme below:

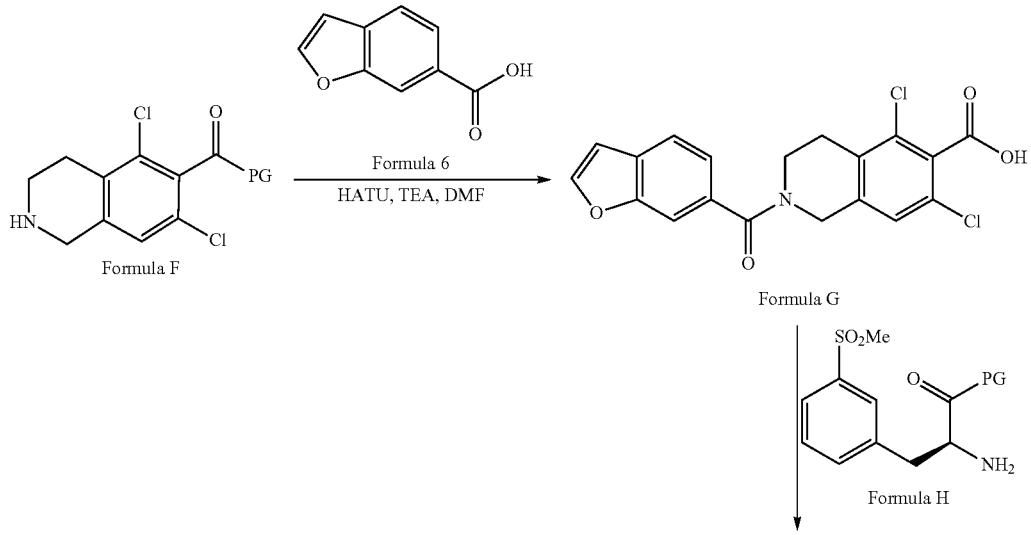

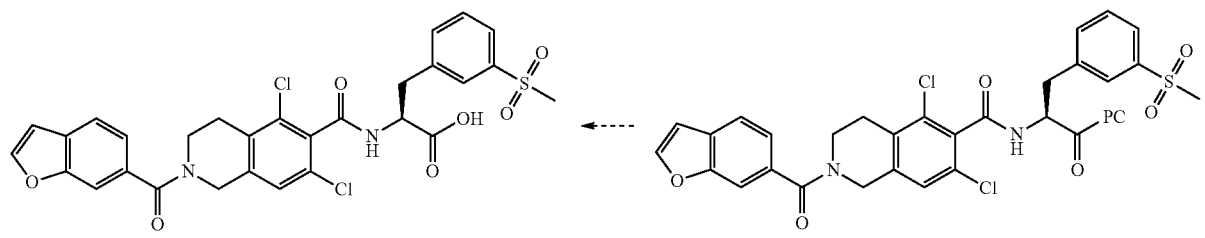

U.S. Pat. No. 9,085,553 also discloses a process of preparing protected lifitegrast of Formula-J by another method as disclosed in the scheme below:

Another object of the present invention is to provide a novel process for the preparation of Lifitegrast which is reproducible and economical for large scale production.

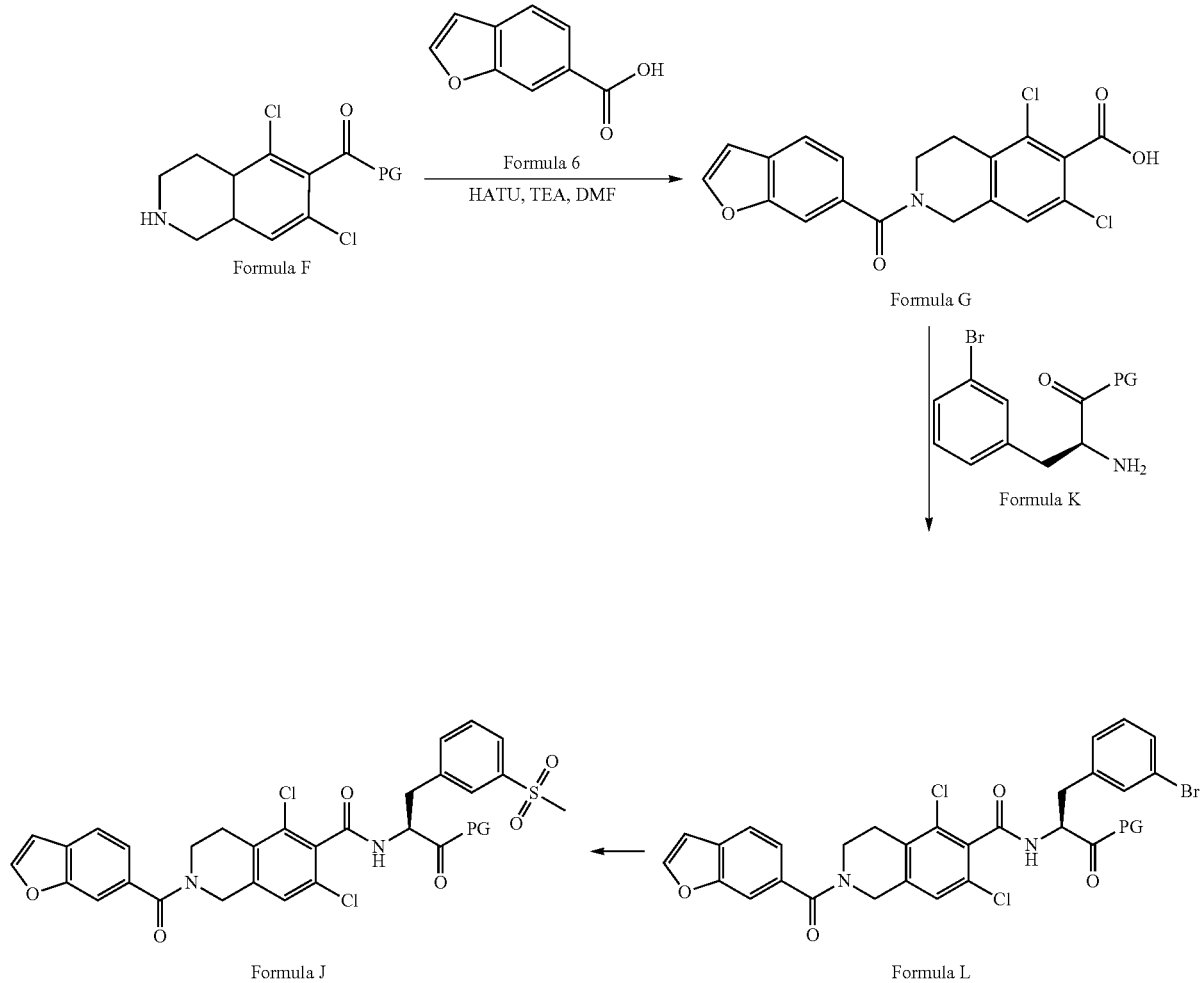

Although, certain published references provides processes of preparation of lifitegrast however, present invention is focussed towards the development of a novel process for the preparation of lifitegrast wherein the process involves less number of steps and hence less number of works ups and purifications resulting into quick and economical process.

Another object of the present invention is to provide a novel purification process of lifitegrast to get pure lifitegrast.

SUMMARY OF THE INVENTION

The main aspect of the present invention provides a process for the preparation of lifitegrast of Formula I.

Formula I

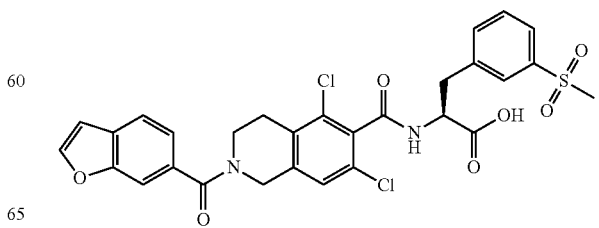

OBJECT OF THE INVENTION

The main aspect of the present invention is to provide a novel process for the preparation of Lifitegrast.

wherein said process comprises the steps of:
a) preparing compound of Formula 2,

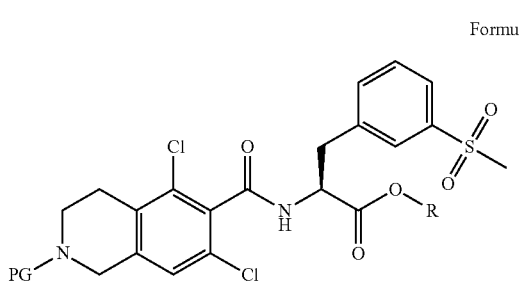

Formula 2 by condensation of protected amine compound of Formula 3 with acid protected compound of Formula 4 or its pharmaceutical acceptable salt,

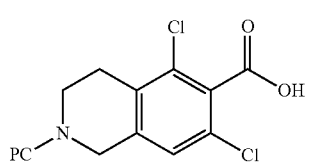

Formula 3

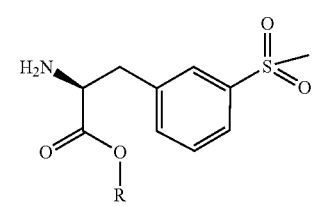

Formula 4 wherein PG is an amine protecting group, and R is an acid protecting group:
b) de-protecting amine group of compound of Formula 2 followed by hydrolysis to give compound of Formula 5;

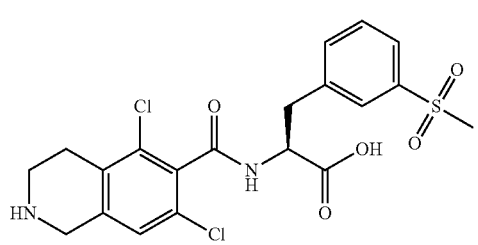

Formula 5 c) optionally purifying compound of Formula 5;
d) condensing compound of Formula 5 with benzofuran-6-carbonyl chloride in presence of base in a solvent to give lifitegrast of Formula I; and
e) optionally purifying the lifitegrast of Formula I.

In another aspect, the present invention provides a novel process for purification of lifitegrast of Formula I,

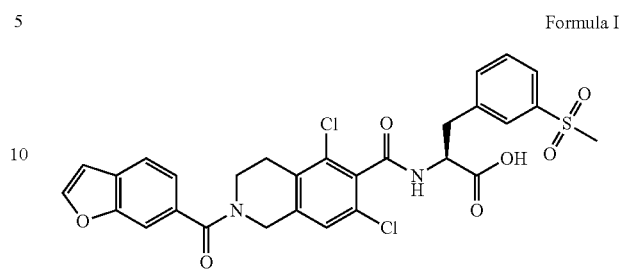

Formula I wherein said process comprises the steps of:
(a) adding crude lifitegrast to a solvent system comprising one or more solvent wherein at least one solvent is water;
(b) adding a base to the solvent system to form a salt of lifitegrast;
(c) adjusting pH between 2 to 5 to get precipitates; and
(d) isolating the precipitates and optionally recrystallizing to get lifitegrast.

Another aspect of the present invention is to prepare substantially pure lifitegrast by reacting (S)-2-(5,7-dichloro-1,2,3,4-tetrahydroisoquinoline-6-carboxamido)-3-(3-(methylsulfonyl)phenyl)propanoic acid of Formula 5 with benzofuran-6-carbonyl chloride, wherein said compound of Formula 5 is characterized by X-Ray powder diffraction pattern comprising peaks at about 9.55, 12.44, 17.93, 19.57, 20.97, 23.98±0.2°2θ.

DETAILED DESCRIPTION

Drawings

Figure 2:
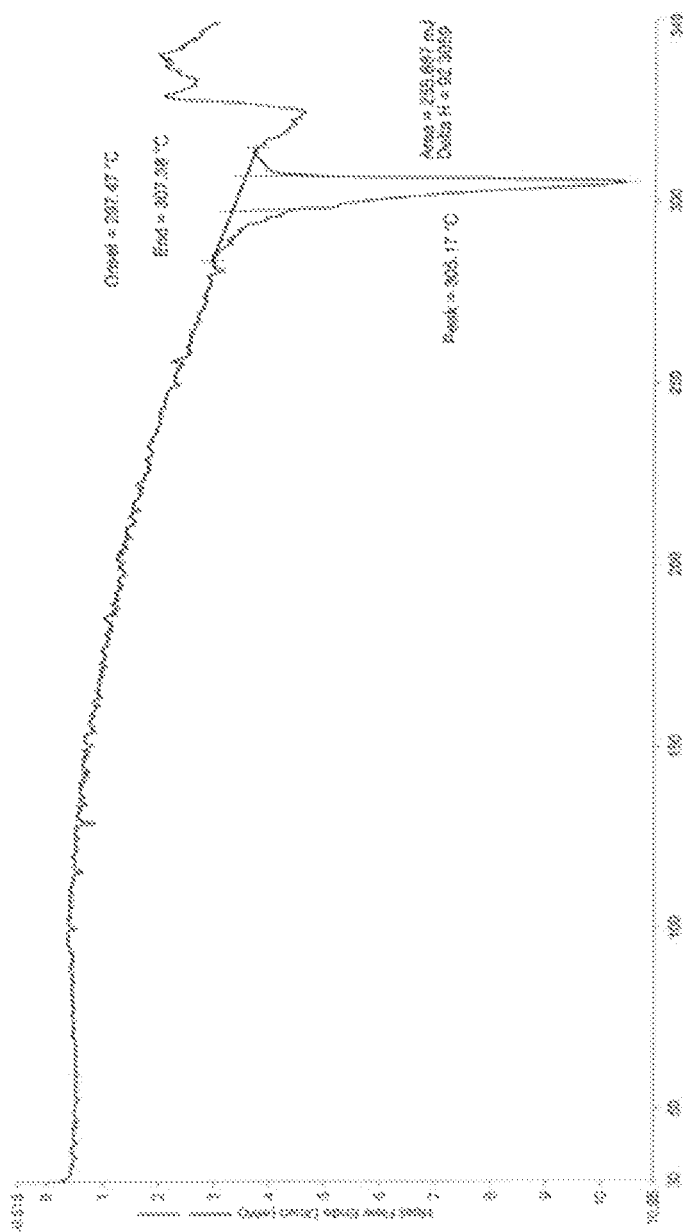

FIG. 1 represents X-ray powder diffraction pattern of compound of Formula 5
FIG. 2 represents Differential Scanning Calorimetry of compound of Formula 5

DEFINITIONS

As used herein, the phrase "amine protecting group" means temporary substituents which protect a potentially reactive amino functional group from undesired chemical transformations.

As used herein, the phrase "acid protecting group" means temporary substituents which protect a potentially reactive acid functional group from undesired chemical transformations.

It must be noted that, as used in the specification and the appended claims, the singular forms "a," "an" and "the" include plural referents unless the context clearly dictates otherwise. Thus, for example, reference to "a solvent" includes mixtures of solvents.

"Optional" or "optionally" means that the subsequently described event or circumstance may or may not occur, and that the description includes instances where said event or circumstance occurs and instances where it does not.

The present invention will now be explained in details. While the invention is susceptible to various modifications and alternative forms, specific embodiment thereof will be described in detail below. It should be understood, however that it is not intended to limit the invention to the particular forms disclosed, but on the contrary, the invention is to cover all modifications, equivalents, and alternative falling within the scope of the invention as defined by the appended claims.

The steps of a method may be providing more details that are pertinent to understanding the embodiments of the present invention and so as not to obscure the disclosure with details that will be readily apparent to those of ordinary skill in the art having benefit of the description herein.

Further characteristics and advantages of the process according to the invention will result from the description herein below of preferred exemplary embodiments, which are given as indicative and non-limiting examples.

Accordingly, in one embodiment, the present invention provides a process of preparation of lifitegrast of Formula I.

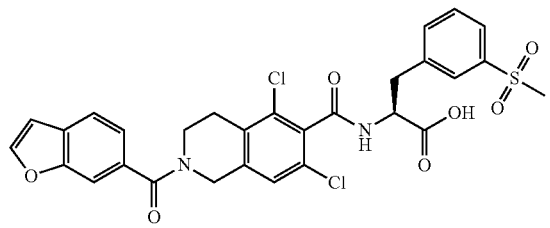

wherein said process comprises the steps of:
a) preparing compound of Formula 2,

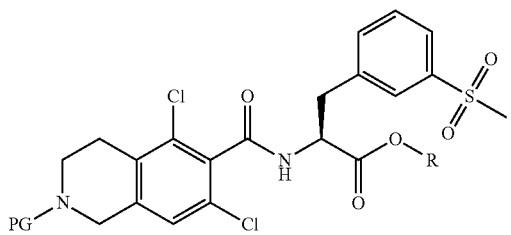

by condensation of protected amine compound of Formula 3 with acid protected compound of Formula 4 or its pharmaceutical acceptable salt,

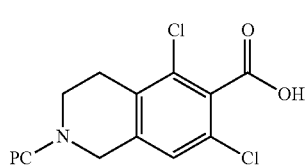

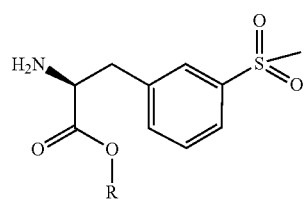

wherein PG is an amine protecting group, and R is an acid protecting group;
b) de-protecting amine group of compound of Formula 2 followed by hydrolysis to give compound of Formula 5;

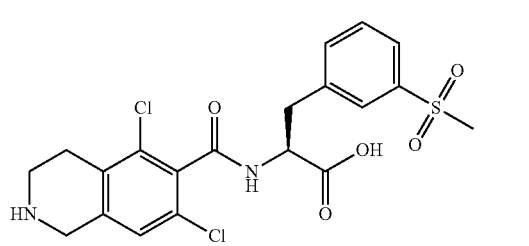

c) optionally purifying compound of Formula 5;
d) condensing compound of Formula 5 with benzofuran-6-carbonyl chloride in presence of base in a solvent to give lifitegrast of Formula I; and
e) optionally purifying the lifitegrast of Formula I.

In another embodiment, the base used in preparation of lifitegrast is selected from the group comprising of primary amines, secondary amines, tertiary amines and inorganic amines. Preferably, the base used for condensing compound of Formula 5 with benzofuran-6-carbonyl chloride is selected from diisopropyl ethyl amine, pyridine, triethyl amine, dimethyl amino pyridine, potassium hydroxide, sodium hydroxide, lithium hydroxide, sodium carbonate, sodium bicarbonate, potassium carbonate, potassium bicarbonate, and cesium carbonate.

In another embodiment, the benzofuran-6-carbonyl chloride of Formula 7 is prepared by treating benzofuran-6-carboxylic acid of Formula 6 with acylating agent in presence of aprotic solvent.

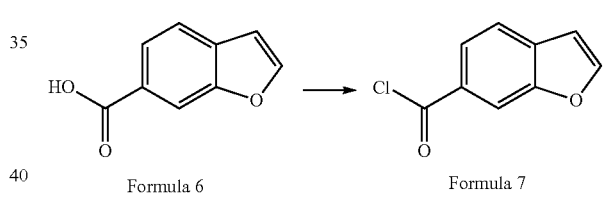

In another embodiment, the acylating agent is selected from thionyl chloride, oxalyl chloride, phosphorus pentachloride, and phosphoryl chloride.

In other embodiment, the condensation of compound of Formula 3 with compound of Formula 4 is performed in a reaction mixture comprising of condensing agent, base and an organic solvent.

In a preferred embodiment, the condensing agent selected from the group comprising of 1-Ethyl-3-(3-dimethylaminopropyl)carbodiimide (EDC), N,N'-Dicyclohexylcarbodiimide (DCC), N-[(Dimethylamino)-1H-1,2,3-triazolo-[4,5-b]pyridin-1-ylmethylene]-N-methylmethanaminium hexafluorophosphate N-oxide (HATU), Hydroxybenzotriazole (HOBt), Hexafluorophosphate Benzotriazole Tetramethyl Uronium (HBTU), O-(Benzotriazol-1-yl)-N,N,N',N'-tetramethyluronium tetrafluoroborate (TBTU), and the like.

In another preferred embodiment, the base used for condensing compound of Formula 3 with compound of Formula 4 is selected from dimethyl amino pyridine (DMAP), triethyl amine (TEA), diisopropyl ethyl amine (DIPEA), 2,4,6-collidine, 1,3,5-collidine and the like.

In another embodiment, the solvent used for preparation of lifitegrast is selected from polar aprotic solvents such as dimethyl formamide (DMF), dimethyl acetamide (DMAc), N-methyl pyrrolidinone (NMP), and dimethyl sulfoxide (DMSO); halogenated solvents such as dichloromethane (DCM), dichlorobenzene, dichloroethane; esters such as ethyl acetate (EtOAc), n-butyl acetate, isopropyl acetate, n-propyl acetate, propenyl acetate, pentyl acetate; ethers such as diethyl ether, tetrahydrofuran (THF), dioxane, methyl tetrahydrofuran (Me-THF); ketones such as acetone, methyl ethyl ketone, methyl isobutyl ketone; organic amines such as secondary and tertiary amines; other solvents such as acetonitrile, xylene, toluene water, and mixture thereof.

In a preferred embodiment, the above said solvent is selected from the solvents other than alcohols and each solvent used in the above said process is free from alcohol.

In a preferred embodiment, the solvent used for condensation of compound of Formula 3 with compound of Formula 4 is selected from polar aprotic solvents such as dimethyl formamide (DMF), dimethyl acetamide (DMAc), N-methyl pyrrolidinone (NMP), and dimethyl sulfoxide (DMSO) and most preferably, dimethyl formamide.

In another preferred embodiment, the solvent used for condensing benzofuran-6-carbonyl chloride of Formula 7 with (S)-2-(5,7-dichloro-1,2,3,4-tetrahydroisoquinoline-6-carboxamido)-3-(3-(methylsulfonyl)phenyl)propanoic acid of Formula 5 is selected from dichloromethane (DCM), dichlorobenzene, dichloroethane, ethyl acetate (EtOAc), n-butyl acetate, isopropyl acetate, n-propyl acetate, propenyl acetate, pentyl acetate, acetonitrile, water or mixture thereof. Most preferably, the solvent used in above said condensation reaction is dichloromethane.

In further embodiment, the base used for condensing benzofuran-6-carbonyl chloride of Formula 7 with (S)-2-(5,7-dichloro-1,2,3,4-tetrahydroisoquinoline-6-carboxamido)-3-(3-(methylsulfonyl)phenyl)propanoic acid of Formula 5 is selected from dimethyl amino pyridine (DMAP), triethyl amine (TEA), diisopropyl ethyl amine (DIPEA), 2,4,6-collidine, 1,3,5-collidine, sodium hydroxide, potassium hydroxide, cesium hydroxide, lithium hydroxide, sodium carbonate, sodium bicarbonate, potassium carbonate, potassium bicarbonate, cesium carbonate, cesium bicarbonate and the like.

In another embodiment, the process of de-protection of amine group of compound of Formula 2 is performed in presence of acid and solvent wherein said acid is selected from dilute hydrochloric acid, dioxane hydrochloric acid, methanesulfonic acid, and trifluoro acetic acid.

In another embodiment, the solvent used for conducting deprotection of amine group of compound of Formula 2 is selected from diethyl ether, tetrahydrofuran (THF), dioxane, methyl tetrahydrofuran (Me-THF), acetone, methyl ethyl ketone, methyl isobutyl ketone, toluene, acetonitrile and mixture thereof.

In further embodiment, deprotection of amine group of compound of Formula 2 results into preparation of compound of Formula 14 which upon hydrolysis in presence of base and solvent results into preparation of compound of Formula 5.

In a preferred embodiment, the base used for hydrolysis of compound of Formula 14 is selected from ammonia, diethyl amine, triethyl amine, methyl amine, dimethyl aminopyridine, pyridine, sodium hydroxide, potassium hydroxide, cesium hydroxide, lithium hydroxide, carbonates and bicarbonates of alkali and alkaline earth metals, and the like.

In another preferred embodiment, the solvent used for conducting hydrolysis of compound of Formula 14 is selected from diethyl ether, tetrahydrofuran (THF), dioxane, methyl tetrahydrofuran (Me-THF), acetone, methyl ethyl ketone, methyl isobutyl ketone, acetonitrile, water and mixture thereof.

In further embodiment, the compound of Formula 5 may be purified before proceeding to next step of condensation with compound of Formula 7 to get lifitegrast.

In another embodiment, the present invention provides a process of preparation of lifitegrast of Formula I,

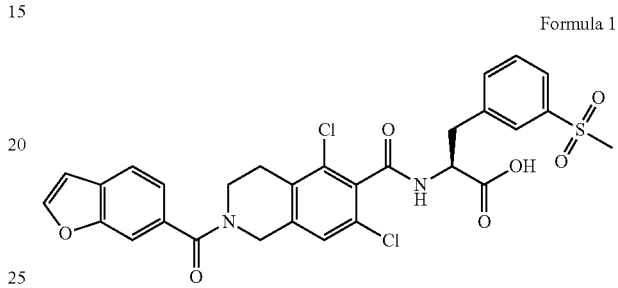

Formula 1 wherein said process comprises the steps of:
a) preparing compound of Formula 2,

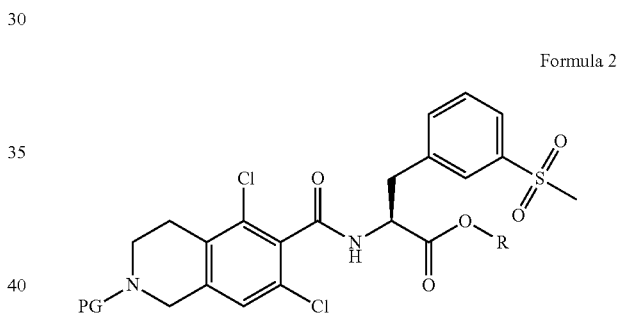

Formula 2 by condensation of protected amine compound of Formula 3 with acid protected compound of Formula 4 or its pharmaceutical acceptable salt,

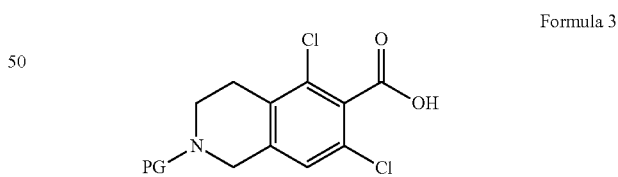

Formula 3

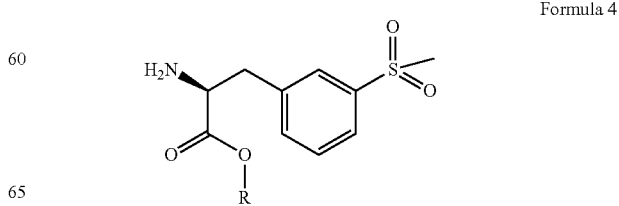

Formula 4 wherein PG is an amine protecting group, and R is an acid protecting group;

b) de-protecting amine group of compound of Formula 2 in presence of acid followed by hydrolysis in presence of base, in absence of alcohol to give compound of Formula 5;

Formula 5

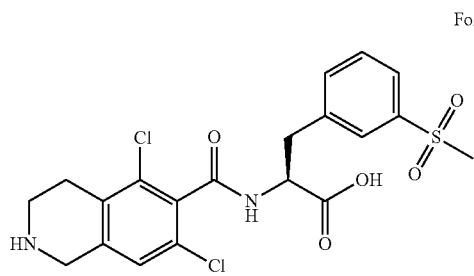

c) purifying compound of Formula 5 in a solvent free from alcohol;
d) condensing compound of Formula 5 with benzofuran-6-carbonyl chloride in presence of base in a solvent to give lifitegrast of Formula I; and
e) optionally purifying lifitegrast of Formula I.

In one another embodiment, the present invention provides a novel process for the preparation of lifitegrast of Formula I, wherein said process comprises the steps of:
a) preparation of 2-(benzofuran-6-carbonyl)-5,7-dichloro-1,2,3,4-tetrahydroisoquinoline-6-carboxylic acid of Formula 9, Formula 9

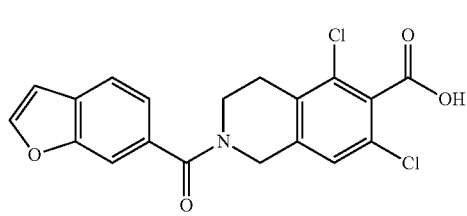

by condensation of benzofuran-6-carbonyl chloride of Formula 7 with 5,7-dichloro-1,2,3,4-tetrahydroisoquinoline-6-carboxylic acid of Formula 8 in presence of acylating agent and base;

Formula 8

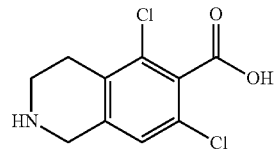

b) condensation of compound of Formula 9 with (S)-2-amino-3-(3-(methylsulfonyl)phenyl)propanoic acid of Formula 10 or its pharmaceutical acceptable salt.

Formula 10

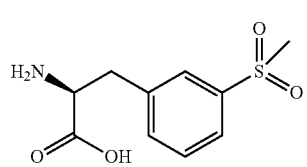

to give lifitegrast of Formula I; and
c) optionally purifying lifitegrast of Formula I.

As per the present invention, lifitegrast can be prepared by two alternative methods as mentioned under scheme 4 and 5 respectively, wherein both methods involves less number of reaction steps and hence, involves minimum loss of solvents in purification and work ups.

Scheme-4

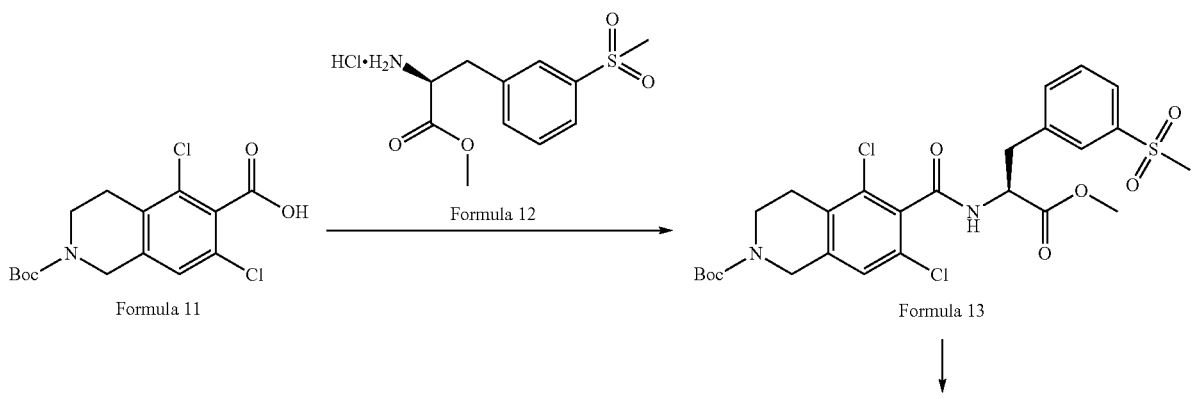

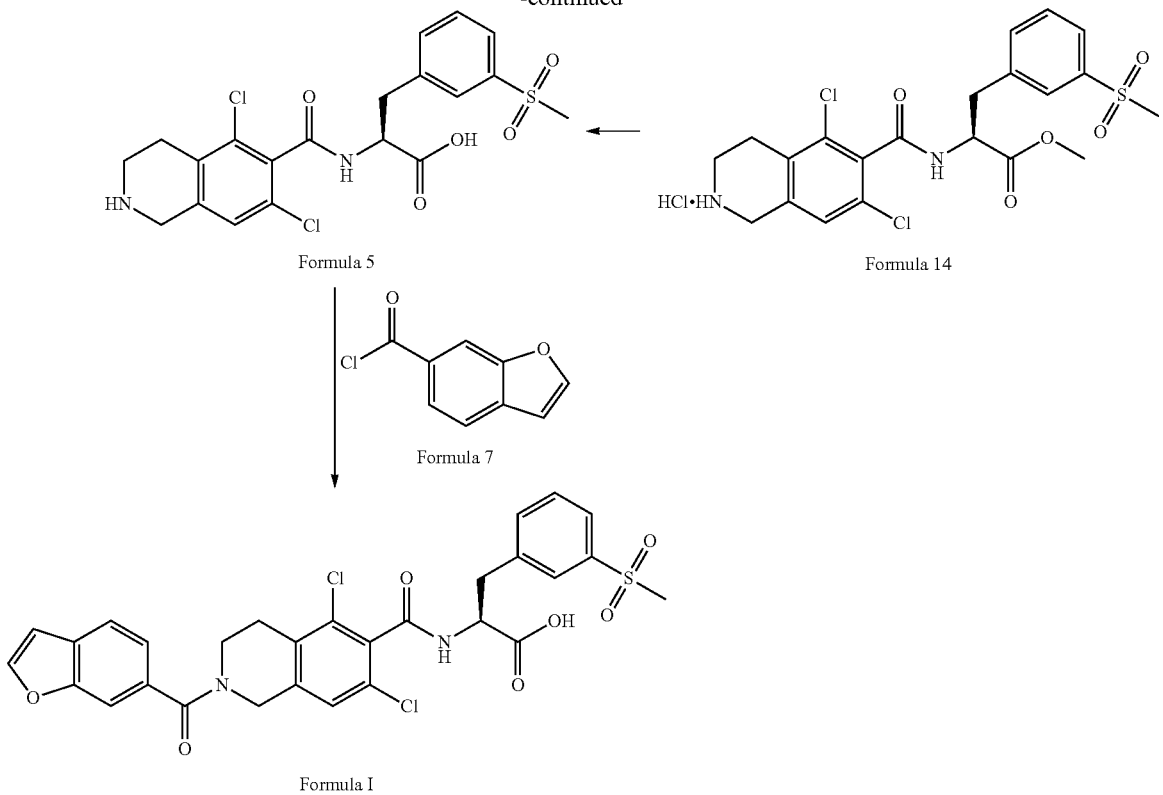

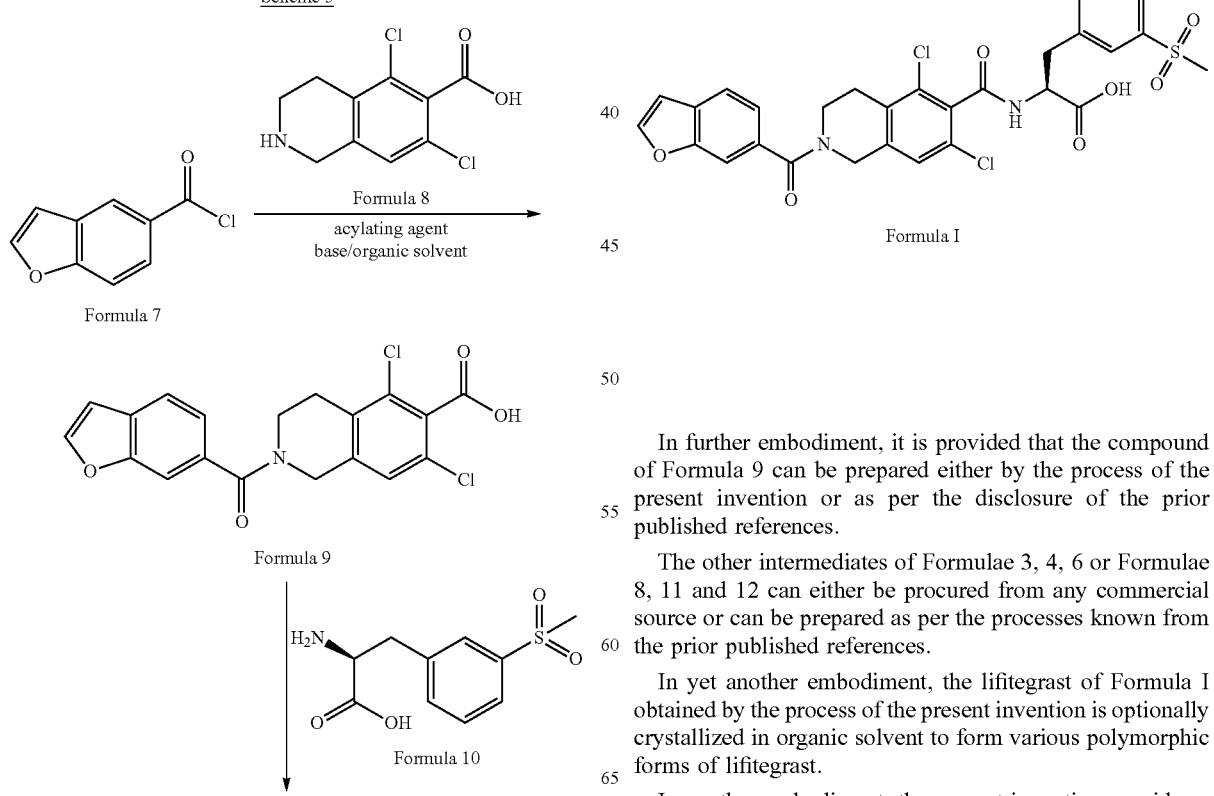

In further embodiment, it is provided that the compound of Formula 9 can be prepared either by the process of the present invention or as per the disclosure of the prior published references.

The other intermediates of Formulae 3, 4, 6 or Formulae 8, 11 and 12 can either be procured from any commercial source or can be prepared as per the processes known from the prior published references.

In yet another embodiment, the lifitegrast of Formula I obtained by the process of the present invention is optionally crystallized in organic solvent to form various polymorphic forms of lifitegrast.

In another embodiment, the present invention provides a novel process for purification of lifitegrast of Formula I,

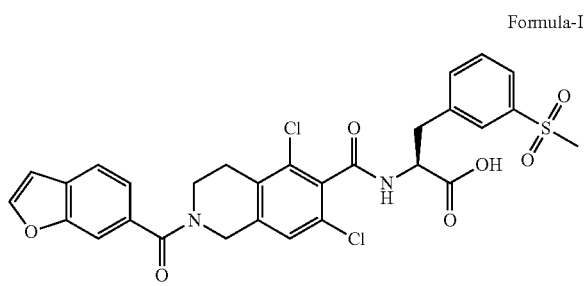 [SMILES: CS(=O)(=O)c1cccc(C[C@H](NC(=O)c2c(Cl)cc3c(c2Cl)CCN(C(=O)c2ccc4ccoc4c2)C3)C(=O)O)c1]

Formula-I wherein said process comprises the steps of:
(a) adding crude lifitegrast to a solvent system comprising one or more solvent wherein at least one solvent is water;
(b) adding a base to the solvent system to form a salt of lifitegrast;
(c) adjusting pH between 2 to 5 to get precipitates; and
(d) isolating the precipitates and optionally recrystallizing to get lifitegrast.

In another embodiment, the solvent system comprises of one or more solvents wherein at least one solvent is water. Moreover the solvents are selected from the group comprising of halogenated solvents such as dichloromethane (DCM), dichlorobenzene, dichloroethane; esters such as ethyl acetate (EtOAc), n-butyl acetate, isopropyl acetate, n-propyl acetate, propenyl acetate, pentyl acetate; ethers such as diethyl ether, tetrahydrofuran (THF), dioxane, methyl tetrahydrofuran (Me-THF), methyl ethyl ether; ketones such as acetone, methyl ethyl ketone; organic amines such as secondary and tertiary amines; other solvents such as acetonitrile, xylene, toluene, water, and mixture thereof.

In a preferred embodiment, the solvent system consists of water and/or solvent selected from dichloromethane, ethyl acetate, n-butyl acetate, propenyl acetate, acetone, methyl ethyl ketone, tetrahydrofuran, diethyl ether, methyl ethyl ether, and acetonitrile.

In another embodiment, the base used for preparing lifitegrast salt is selected from primary amines, secondary amines, and alkali metal bases. Preferably the base is selected from diisopropyl ethyl amine, ethanolamine, meglumine, piperidine, benzyl piperazine, diethyl amine, methyl benzyl amine, morpholine, N, N-dibenzyl ethylene diamine, sodium hydroxide, potassium hydroxide, and lithium hydroxide.

In another embodiment, the precipitates of lifitegrast are isolated by a process such as filtration, concentration, centrifugation, decantation of solvent, lyophilisation, or by any known conventional method.

Another embodiment of the present invention provides a process of preparing substantially pure lifitegrast by reacting (S)-2-(5,7-dichloro-1,2,3,4-tetrahydroisoquinoline-6-carboxamido)-3-(3-(methylsulfonyl)phenyl)propanoic acid of Formula 5 with benzofuran-6-carbonyl chloride, wherein said compound of Formula 5 is characterized by X-ray powder diffraction pattern comprising peaks at about 9.55, 12.44, 17.93, 19.57, 20.97, 23.98±0.2°2θ.

In another embodiment, the present invention provides crystalline (S)-2-(5,7-dichloro-1,2,3,4-tetrahydroisoquinoline-6-carboxamido)-3-(3-(methylsulfonyl) phenyl)propanoic acid of Formula 5, characterized by X-Ray powder diffraction pattern comprising peaks at about 9.55, 12.44, 17.93, 19.57, 20.97, 23.98±0.2°2θ.

In a preferred embodiment, (S)-2-(5,7-dichloro-1,2,3,4-tetrahydroisoquinoline-6-carboxamido)-3-(3-(methylsulfonyl)phenyl)propanoic acid of Formula 5 is characterized by X-ray powder diffraction pattern consisting peaks at about 4.71, 9.55, 10.36, 12.44, 12.81, 16.22, 17.93, 19.00, 19.57, 20.16, 20.97, 21.39, 22.48, 23.12, 23.98, 26.39, 30.14, 31.73, 33.33, and 36.88±0.2°θ.

In another preferred embodiment, (S)-2-(5,7-dichloro-1,2,3,4-tetrahydroisoquinoline-6-carboxamido)-3-(3-(methylsulfonyl)phenyl)propanoic acid of Formula 5 is characterized by Differential Scanning Calorimetry (DSC) plot having peak onset at about 297.47° C. and endotherm peak at about 305.17° C.

In further embodiment, the present invention further relates to a composition comprising lifitegrast of Formula I obtained by the process of the present invention along with at least one pharmaceutically acceptable excipients thereof.

In one more embodiment, present invention provides use of compound of Formula I as prepared by the process of the present invention, as a LFA-1 inhibitor and for the treatment of dry eye disease.

In other embodiment, the lifitegrast as prepared by the process of the present invention is isolated with purity of 98% and above and preferably, 99% and above and most preferably with purity of 99.9% and above.

In another embodiment, the lifitegrast as prepared by the process of the present invention is characterized by particle size distribution wherein, $d_{90}$ is 0.1 μm to 200 μm.

In a preferred embodiment, the lifitegrast as prepared by the process of the present invention is characterized by particle size distribution wherein, $d_{90}$ is 2.0 μm to 150 μm.

The present invention is explained below by way of examples. However, the examples are provided as one of the possible way to practice the invention and should not be considered as limitation of the scope of the invention.

EXAMPLES

Example 1: Synthesis of 4-(3-bromobenzylidene)-2-methyl-1,3-oxazol-5(4H)-one

Charged 300 g of acetic anhydride to 185 g of 3-Bromo benzaldehyde and sodium acetate 10 gm. Temperature of reaction mass was raised to 95-100° C. followed by addition of 117 g of N-acetyl glycine. Reaction mass was stirred at 90-95° C. and after completion of reaction, the reaction mass was cooled to 70-75° C. Acetic anhydride was distilled under reduced pressure and methanol (500 ml) was added. Reaction mass was cooled to ambient temperature and filtered the precipitated solid to get 210 g of 4-(3-bromobenzylidene)-2-methyl-1,3-oxazol-5(4H)-one (80% yield)

Example 2: Synthesis of 2-methyl-4-(3-(methylsulfonyl)benzylidene)oxazol-5(4H)-one To 200 g of 4-(3-bromobenzylidene)-2-methyl-1,3-oxazol-5(4H)-one and 50 g of copper iodide in 600 ml NMP was added 230 g of sodium methane sulfinate. Temperature of reaction mass was raised to 95-100° C. Reaction mass stirred till completion of reaction and then cooled to room temperature. Added DM Water 2000 ml and filtered to give 170 g of 2-methyl-4-(3-(methylsulfonyl)benzylidene)oxazol-5 (4H)-one (yield—85%)

Example 3: Synthesis of 2-acetamido-3-(3-(methylsulfonyl)phenyl)propanoic Acid

To 150 g of 2-methyl-4-(3-(methylsulfonyl)benzylidene) oxazol-5(4H)-one and 80 g of NaOH charged 2000 ml of water followed by addition of 30 g of Raney Nickel. Hydrogen gas purged and temperature of reaction mass was raised to 60° C. Reaction mass was stirred till consumption of hydrogen gas. Reaction mass was analysed by TLC. Reaction mass was then filtered and pH of mother liquor was adjusted to acidic pH to get the solid of 2-acetamido-3-[3-(methylsulfonyl)phenyl]propanoic acid. Reaction mass was filtered and solid dried under reduced pressure to get 104 g of 2-acetamido-3-(3-(methylsulfonyl)phenyl)propanoic acid (Yield—65%)

Example 4: Synthesis of (2S)-2-acetamido-3-(3-(methylsulfonyl)phenyl)propanoic Acid Cinchonidine Salt Cinchonidine 82 g added to the solution of 100 g of 2-acetamido-3-(3-(methylsulfonyl)phenyl)propanoic acid in 100 ml water and 900 ml methanol. Temperature was raised to 55-65° C. Reaction mass was gradually cooled to 20-25° C. Stirred and filtered to get solid of cinchonidine salt. Crude wad recrystallized in methanol and water to get 64 g of (2S)-2-acetamido-3-(3-(methylsulfonyl)phenyl)propanoic acid cinchonidine salt (Yield—31.5%)

Example 5: Synthesis of (S)-2-amino-3-(3-(methylsulfonyl)phenyl)propanoic Acid 60 g of (2S)-2-acetamido-3-(3-(methylsulfonyl)phenyl) propanoic acid cinchonidine salt was charged in 300 ml of water and pH of reaction mass was adjusted to acidic pH using conc. HCl. Temperature of reaction mass was raised to 50-55° C. After complete deacetylation, pH of reaction mass was adjusted to 50-5.5 using aq. NaOH solution. Filtered the solid to get 21 g of (S)-2-amino-3-(3-(methylsulfonyl)phenyl)propanoic acid (Yield—85%)

Example 6: Synthesis of methyl (S)-2-amino-3-(3-(methylsulfonyl)phenyl)propanoate Hydrochloride 20 g of (S)-2-amino-3-(3-(methylsulfonyl)phenyl)propanoic acid was charged in 100 ml Methanol and reaction mass cooled to 0-5° C. Thionyl chloride (12 g) was added drop wise below 10° C. and reaction mass was stirred at room temperature. After completion of reaction, solvents were distilled under vacuum followed by addition of isopropyl ether (100 ml) and filtered the solid to get 23 g of methyl (S)-2-amino-3-(3-(methylsulfonyl)phenyl)propanoate hydrochloride (Yield—95%)

Example 7: Synthesis of tert-butyl 5,7-dichloro-6-hydroxy-3,4-dihydroisoquinoline-2(1H)-carboxylate 3-methoxyphenylethylamine (50.0 g) and formaldehyde (12.0 g) were added in conc. HCl (500 mL) and the reaction mass was heated at 70-80° C. After completion of reaction, the reaction mass was concentrated and residue dissolved in aqueous hydrobromic acid (100 ml). Reaction mass was heated to 100-105° C. After completion of reaction, reaction mass was basified with sodium carbonate aqueous solution and added t-butanol (200 ml) and Boc-anhydride (120 g) followed by stirring till completion of reaction. Reaction mass was extracted with MDC (200 ml) twice. Organic layer was dried over magnesium sulphate. Acetic acid (200 ml) and sulfuryl chloride (100 g) were then added to organic layer and stirred at RT. After completion of reaction, reaction mass was completely distilled under vacuum. Boc anhydride 120 g, DM water 200 ml and t-butanol 200 ml were added to reaction mass. Once reaction completed, reaction mass was extracted with MDC twice. Organic layer distilled and residue was purified using column chromatography to obtain 34 g of tert-butyl 5,7-dichloro-6-hydroxy-3,4-dihydroisoquinoline-2(1H)-carboxylate.

Example 8: Synthesis of tert-butyl 5,7-dichloro-6-((trifluoromethyl)sulfonyl)-3,4-dihydroisoquinoline-2(1H)-carboxylate 30 g of tert-butyl 5,7-dichloro-6-hydroxy-3,4-dihydroisoquinoline-2(1H)-carboxylate was dissolved in MDC (100 ml) and pyridine (30 mL). Reaction mass was cooled to −20° C. and triflic anhydride (32 g) was added drop wise. Reaction mass stirred at ambient temperature. After completion of reaction, reaction mass was diluted with water 100 ml and layers were separated. Organic layer washed with brine and sodium carbonate solution. Organic layer distilled to get residue of tert-butyl 5,7-dichloro-6-((trifluoromethyl)sulfonyl)-3,4-dihydroisoquinoline-2(1H)-carboxylate compound.

Example 9: Synthesis of 2-(tert-butyl) 6-methyl 5,7-dichloro-3,4-dihydroisoquinoline-2,6(1H)-dicarboxylate To 10 g of tert-butyl 5,7-dichloro-6-[(trifluoromethyl)sulfonyl]-3,4-dihydroisoquinoline-2(1H)-carboxylate, 10 gm of 1,3-di phenyl phosphine propane and 20 ml of di isopropyl ethylamine in 25 ml N,N-dimethyl acetamide and 10 ml methanol was added Palladium acetate 0.5 g and purged carbon monoxide gas through reaction mass. Reaction mass was stirred at ambient temperature to complete consumption of triflate compound. Then reaction mass was concentrated and purified by column chromatography to get 2-tert-butyl 6-methyl 5,7-dichloro-3,4-dihydroisoquinoline-2,6(1H)-dicarboxylate.

Example 10: Synthesis of 2-(tert-butoxycarbonyl)-5,7-dichloro-1,2,3,4-tetrahydroisoquinoline-6-carboxylic Acid 3.0 g of 2-tert-butyl 6-methyl 5,7-dichloro-3,4-dihydroisoquinoline-2,6(1H)-dicarboxylate was charged in mixture of water 20 ml and methanol 5 ml. Solution of 1.0 g lithium hydroxide in water was added and stirred at room temperature. Reaction was monitored by TLC. After completion of reaction mass. pH of reaction mass was adjusted to 5-6 using acetic acid and extracted the reaction mass with MDC 20×2 ml. Organic layer was washed with water and concentrated to get 2-(tert-butoxycarbonyl)-5,7-dichloro-1,2,3,4-tetrahydroisoquinoline-6-carboxylic acid.

Example 11: Synthesis of 1-benzofuran-6-carbaldehyde

A solution of 6-bromo-1-benzofuran (50 g) in tetrahydrofuran (150 ml) was slowly added to isopropylmagnesium bromide (15% in THF, 38 g) at −25° C. After complete of addition the reaction mixture was stirred for 30 min at −25° C. Dimethylformamide (21 g) was added drop wise by maintaining temperature −25° C. Reaction mass was slowly warmed at room temperature. Reaction was monitored by TLC. After completion of reaction, reaction mass was quenched by solution of ammonium chloride. Reaction mass was then extracted in toluene. Separated the toluene layer and concentrated to give 1-benzofuran-6-carbaldehyde compound (30 g) in 80% yield.

Example 12: Synthesis of 1-benzofuran-6-carboxylic Acid 20 g of 1-benzofuran-6-carbaldehyde was charged in solution of 16.5 g of NaOH in 200 ml of water. Temperature was raised to 75-90° C. and treated drop wise with aq. $H_2O_2$ (30%, 18 g) within 2-3 hr. Reaction mass was stirred and monitored till completion of reaction. Reaction mass was acidified and filtered to get 1-benzofuran-6-carboxylic acid in 70% yield.

Example 13: Synthesis of 1-benzofuran-6-carbonitrile

To a solution of 6-bromo-1-benzofuran (30 g) in tetrahydrofuran (150 ml) was added sodium cyanide (22.83 g). Reaction mass was heated to reflux and reaction monitored by TLC. After completion of reaction, reaction mass was diluted with water and Ethyl acetate added to reaction mass. Layers were separated and organic layer was washed with water and brine solution. Organic layer was then separated and concentrated and residue so obtained was purified in column chromatography using ethyl acetate and hexane to get 1-benzofuran-6-carbonitrile. (10.88 g, 50% yield)

Example 14: Synthesis of 1-benzofuran-6-carboxylic Acid 10 g of 1-benzofuran-6-carbonitrile was charged in solution of NaOH (14.0 g) in water (200 ml). Temperature was raised to 90° C. and stirred to complete conversion. Then pH of reaction mass was adjusted to acid pH and precipitated solid was filtered and dried to get 1-benzofuran-6-carboxylic acid. (9.6 g, yield—85.0%)

Example 15: Synthesis of (S)-2-(5,7-dichloro-1,2,3,4-tetrahydroisoquinoline-6-carboxamido)-3-(3-(methylsulfonyl)phenyl)propanoic Acid 2-(tert-butoxycarbonyl)-5,7-dichloro-1,2,3,4-tetrahydroisoquinoline-6-carboxylic acid (20 g), HATU (27.5 g) was charged in DMF (60 ml) and diisopropyl ethylamine (22.2 g) was added. Reaction mass was cooled to 0-5° C. and added methyl (S)-2-amino-3-(3-(methylsulfonyl)phenyl)propanoate hydrochloride (17.6 g) lot wise at 0-5° C. Temperature of reaction mass was raised to room temperature. Stirred and reaction monitored by TLC. After completion of reaction, Water (100 ml) and MDC (100 ml) was added. Stirred and separated the layers. Organic layer washed with brine and 10% sodium carbonate solution. Organic layer distilled and charged 1 N HCl (100 ml) to the residue. After complete hydrolysis pH of reaction mass was adjusted to 5.0-5.5 using sodium hydroxide solution. Reaction mass was filtered and solid so obtained was dried to get (S)-2-(5,7-dichloro-1,2,3,4-tetrahydroisoquinoline-6-carboxamido)-3-(3-(methylsulfonyl)phenyl)propanoic acid (25 g, 91.8% yield).

Example 16: Synthesis of tert-butyl (S)-5,7-dichloro-6-((1-methoxy-3-(3-(methylsulfonyl)phenyl)-1-oxopropan-2-yl)carbamoyl)-3,4-dihydroisouinoline-2(1H)-carboxylate 2-(tert-butoxycarbonyl)-5,7-dichloro-1,2,3,4-tetrahydroisoquinoline-6-carboxylic acid (20.0 g) was added to 50.0 ml of DMF followed by addition of DIPEA (37.2 g), HATU (27.4 g) and stirred the reaction mass for 30 min at room temperature. Charged methyl (S)-2-amino-3-(3-(methylsulfonyl)phenyl)propanoate hydrochloride (17.6 g) and stirred the reaction mass at 100° C. for 1-2 hrs. After completion of reaction, cooled the reaction mass to 30-35° C. charged the reaction mass to the mixture of ethyl acetate (200 ml) and water (200 ml) and stirred for 15-30 min at 30-35° C. Separated the ethyl acetate and washed with acidic water (200 ml water+18 ml of conc. HCl) followed by washing with water. Distilled the ethyl acetate at 40-45° C. to get tert-butyl (S)-5,7-dichloro-6-((1-methoxy-3-(3-(methylsulfonyl)phenyl)-1-oxopropan-2-yl)carbamoyl)-3,4-dihydro isoquinoline-2(1H)-carboxylate (40 g, crude).

Example 17: Synthesis of methyl (S)-2-(5,7-dichloro-1,2,3,4-tetrahydroisoquinoline-6-carboxamido)-3-(3-(methylsulfonyl)phenyl) propanoate Hydrochloride Charged 100 ml of dioxane and 100 ml of dioxane HCl to crude lifitegrast as obtained from example 16 at 25-30° (and stirred for 4-10 h at 25-30° C. After completion of reaction, added methyl isobutyl ketone (300 ml) at 25-30° C. Stirred the reaction mass for 3-4 hr at 25-30° C. and filtered the material followed by washing with 50 ml of methyl isobutyl ketone to get wet material (wet 75-90 g)

Example 18: Synthesis of (S)-2-(5,7-dichloro-1,2,3,4-tetrahydroisoquinoline-6-carboxamido)-3-(3-(methylsulfonyl)phenyl)propanoic Acid Charged 5-10 vol of THF to methyl (S)-2-(5,7-dichloro-1,2,3,4-tetrahydroisoquinoline-6-carboxamido)-3-(3-(methylsulfonyl)phenyl)propanoate hydrochloride at 20-25° C. Cooled the reaction mass to 0-5° C. and added sodium hydroxide solution (2 Vol) (7.0 mol equivalent of sodium hydroxide in 2.0 vol of water) at 0-5° C. Stirred the reaction mass at 25-30° C. for 10-15 hrs. After completion of reaction, separated the aqueous and THF layer at 20-25° C. Added 5-10 Vol of THF and adjusted the pH 7-9 with conc. HCl and stirred the crystallized material for 2-3 h at 20-30° C. Filtered the solid material and washed with THF (2 Vol) and dried the solid material at 50° C. under vacuum to get(S)-2-(5,7-dichloro-1,2,3,4-tetrahydroisoquinoline-6-carboxamido)-3-(3-(methylsulfonyl)phenyl) propanoic acid with 98% yield.

Example 19: Example 18: Synthesis of (S)-2-(5,7-dichloro-1,2,3,4-tetrahydroisoquinoline-6-carboxamido)-3-(methylsulfonyl)phenyl) Propanoic Acid Charged 80 ml of water in methyl (S)-2-(5,7-dichloro-1,2,3,4-tetrahydroisoquinoline-6-carboxamido)-3-(3-(methylsulfonyl)phenyl) propanoate hydrochloride (wet 75-90 g) at 20-25° C. Added 20 ml of sodium hydroxide solution (12.7 g of sodium hydroxide in 20 ml of water) at 20-25° C. Stirred the solution at 20-25° C. for 10-15 hrs and after completion of reaction, distilled out the reaction mass completely under vacuum at 38-42° C. Charged 100 ml of water and stirred for clarity at 20-25° C. Charged 100 ml of dichloromethane and stirred followed by spearing the layers and washing the aqueous layer with dichloromethane. Added carbon to aqueous layer, stirred and filtered to remove carbon. Adjusted the pH of aqueous layer to 3 to 5 by concentrated HCl and stirred for 2-3 hr at 20-25° C. and filtered the solid material. Washed the solid so obtained with water (50 ml) and then dried the solid material at 50° C.

under vacuum to get (S)-2-(5,7-dichloro-1,2,3,4-tetrahydroisoquinoline-6-carboxamido)-3-(3-(methylsulfonyl)phenyl) propanoic acid.

Example 20: Synthesis of Lifitegrast 1-benzofuran-6-carboxylic acid (5.0 g) was charged in dichloromethane and added thionyl chloride (4.5 g) followed by stirring to get clear solution. The solvent was removed under reduced pressure. MDC (20 ml) was charged to the residue. The acid chloride, in methylene chloride was added slowly to a solution of (S)-2-(5,7-dichloro-1,2,3,4-tetrahydroisoquinoline-6-carboxamido)-3-(3-(methyl sulfonyl)phenyl)propanoic acid (13.8 g) and diisopropylethylamine (10 ml) below 5° C. Reaction mass was stirred at 0-5° C. till completion of reaction. Reaction mass was then quenched with water 25 ml. Layers were separated and organic layer washed with sodium bicarbonate solution. Organic layer concentrated to get crude Lifitegrast. Crude lifitegrast was recrystallized in acetone, (13 g, yield—72.8%)

Example 21: Synthesis of Lifitegrast 1-benzofuran-6-carboxylic acid (10 g), HOBt (12.5 g) and EDC.HCl (17.75 g) was charged in THF (60 ml). To this solution was added di isopropyl ethylamine (22.2 g). Reaction mass was cooled to 0-5° C. Added (S)-2-(5,7-dichloro-1,2,3,4-tetrahydroisoquinoline-6-carboxamido)-3-(3-(methyl sulfonyl)phenyl)propanoic acid (28.5 g) lot wise at −10° C. Temperature of reaction mass was raised to room temperature. Stirred and monitored the reaction by TLC. After completion of reaction. Water (100 ml) and MDC (100 ml) were added. Stirred and separated the layers. Organic layer so obtained was washed with brine and 10% sodium carbonate solution. Organic layer was distilled to give crude lifitegrast which was then purified in acetone and methanol to give pure lifitegrast (31.2 g, 83.8%).

Example 22: Synthesis of Lifitegrast

Charged 3.6 g of 1-benzofuran-6-carboxylic acid in dichloromethane and added oxalyl chloride (3.44 g) and stirred for 5-8 hrs at 0-10° C. under nitrogen and added in mixture of (S)-2-(5,7-dichloro-1,2,3,4-tetrahydroisoquinoline-6-carboxamido)-3-(3-(methyl sulfonyl)phenyl)propanoic acid (10.0 g) and sodium hydroxide solution (NaOH 4.24 g+50.0 ml water) in 50 ml of dichloromethane at temperature of −5 to 0° C. Stirred the reaction mass for 30-60 min at −5 to 0° C. After completion of reaction, added conc. HCl solution to adjusted the pH to 1-2. Then stirred the reaction mass for 10-15 minutes. Separated the aqueous and dichloromethane layer. Seeded the dichloromethane layer and stirred for 30 min and then charged acetonitrile (50 ml) and stirred for 10-15 hr at 20-25° C. Filtered the solid material and washed with acetonitrile to get crude lifitegrast (10-12 g).

Example 23: Purification of Lifitegrast

Charged 30 ml of water and 30 ml of dichloromethane to lifitegrast (please provide the amount) and added diisopropyl ethyl amine (1.25 g) and stirred for 30 min. Separated the aqueous layer and organic layer and washed the organic layer with water. Added 20 ml of water in the organic layer and adjusted the pH to 2-5 by dil. hydrochloric acid. Stirred and separate the organic layer followed by concentration under vacuum to get pure Lifitegrast.

Example 24: Purification of Lifitegrast

Charged acetonitrile (150 ml) and 10 g of crude lifitegrast followed by heating to 80-85° C. Stirred the solution at 80-85° C. for 1 h and then slowly cooled to 20-25° C. Stirred for 1-4 hr at 20-25° C. and filtered the solid material followed by washing with acetonitrile (20 ml). Dried the material at 40-450° C. under vacuum for 4-8 hrs.

Example 25: Purification of Lifitegrast

Charged 150 ml of water to 10 g of lifitegrast and added 10% caustic solution. Stirred the reaction mass at room temperature for 1 hr. Added conc. HCl solution to adjust the pH to less than 1.0 at 20-25° C. Stirred for 1-4 hr at 20-25° C. filtered the solid material and washed with water (20 ml). Dried the solid under vacuum at 40-50° C. to get pure lifitegrast.

The invention claimed is:
1. A process for preparing lifitegrast of Formula I,

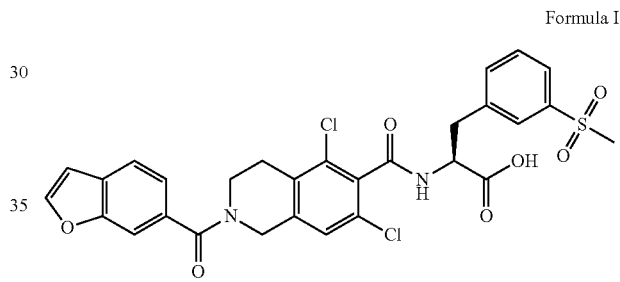

Formula I comprising:
a) preparing a compound of Formula 2,

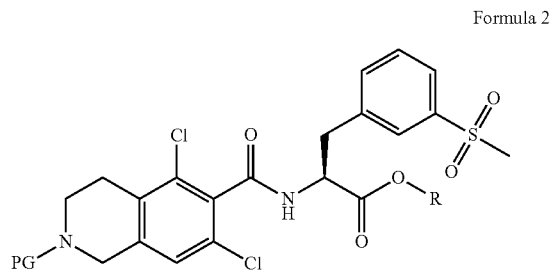

Formula 2 by condensation of a protected amine compound of Formula 3 with an acid protected compound of Formula 4 or pharmaceutical acceptable salt thereof,

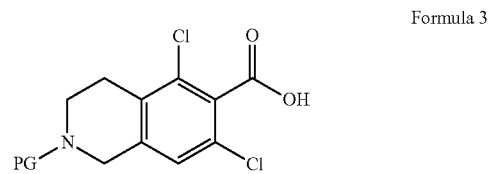

Formula 3

-continued

Formula 4

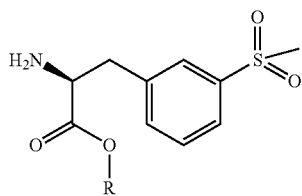

wherein PG is an amine protecting group, and R is an acid protecting group;

b) de-protecting amine group of the compound of Formula 2 followed by hydrolysis to give a compound of Formula 5;

Formula 5

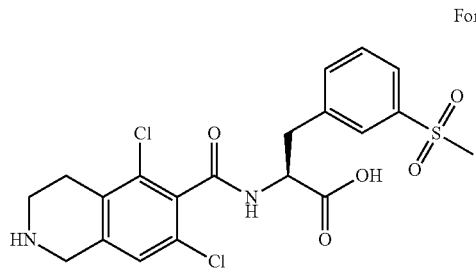

c) optionally purifying the compound of Formula 5;

d) condensing the compound of Formula 5 with benzofuran-6-carbonyl chloride in presence of a base in a solvent to give the lifitegrast of Formula I; and e) optionally purifying the lifitegrast of Formula I.

2. The process as claimed in claim 1, wherein said base is at least one base selected from the group consisting of dimethyl amino pyridine (DMAP), triethyl amine (TEA), diisopropyl ethyl amine (DIPEA), 2,4,6-collidine, 1,3,5-collidine, sodium hydroxide, potassium hydroxide, cesium hydroxide, lithium hydroxide, sodium carbonate, sodium bicarbonate, potassium carbonate, potassium bicarbonate, cesium carbonate, and cesium bicarbonate.

3. The process as claimed in claim 1, wherein said solvent is a solvent selected from the group consisting of dichloromethane (DCM), dichlorobenzene, dichloroethane, ethyl acetate (EtOAc), n-butyl acetate, isopropyl acetate, n-propyl acetate, propenyl acetate, pentyl acetate, acetonitrile, water, and mixtures thereof.

4. The process as claimed in claim 1, wherein said solvent is free from alcohol.

5. Crystalline form of a compound of Formula 5 characterized by X-ray powder diffraction pattern comprising peaks at about 9.55, 12.44, 17.93, 19.57, 20.97, 23.98±0.2°2θ, Formula 5

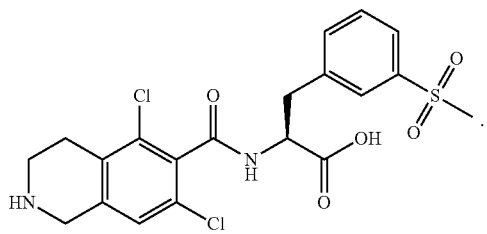

6. The process as claimed in claim 1,
wherein said de-protection of amine group of the compound of Formula 2 is carried out in presence of at least one acid selected from the group consisting of dilute hydrochloric acid, dioxane hydrochloric acid, methanesulfonic acid, and trifluoro acetic acid, and
wherein said hydrolysis is carried out in presence of at least one base selected from the group consisting of ammonia, diethyl amine, triethyl amine, methyl amine, dimethyl aminopyridine, pyridine, sodium hydroxide, potassium hydroxide, cesium hydroxide, lithium hydroxide, carbonates, and bicarbonates of alkali and alkaline earth metals.

\* \* \* \* \*